United States Patent
Sittek et al.

(10) Patent No.: US 6,270,506 B1
(45) Date of Patent: Aug. 7, 2001

(54) MEDICAL TARGETING APPARATUS

(75) Inventors: Harald Sittek, Grafrath; Erwin Linsmeier, Munich, both of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/365,665

(22) Filed: Aug. 2, 1999

(30) Foreign Application Priority Data

Jul. 31, 1998 (DE) .............................................. 198 34 586

(51) Int. Cl.⁷ .................................................... A61B 19/00
(52) U.S. Cl. ............................................................. 606/130
(58) Field of Search ....................................... 600/427, 429, 600/227; 378/37; 606/130, 129; 604/116

(56) References Cited

U.S. PATENT DOCUMENTS

| | | |
|---|---|---|
| 4,629,989 | 12/1986 | Riehl et al. . |
| 4,875,478 * | 10/1989 | Chen ................................. 606/130 |
| 5,056,523 | 10/1991 | Hotchkiss, Jr. et al. . |
| 5,678,549 | 10/1997 | Heywang-Koebrunner et al. . |
| 5,730,745 | 3/1998 | Schulte et al. . |
| 5,876,332 * | 3/1999 | Looney ................................. 600/227 |

FOREIGN PATENT DOCUMENTS

| | | |
|---|---|---|
| 0 752 237 | 1/1997 | (EP) . |
| 752237 * | 1/1997 | (EP) ................................ 606/130 |

* cited by examiner

*Primary Examiner*—Pedro Philogene
(74) *Attorney, Agent, or Firm*—Schiff Hardin & Waite

(57) ABSTRACT

A medical targeting apparatus has assembly composed of several parts arranged so as to be able to be displaced relative to one another, an instrument control unit fastened to the assembly an adjustment arrangement for adjusting the parts and the instrument control unit relative to one another, a patient mount for positioning at least a body part of a patient in a diagnostic imaging apparatus, and a marking device, connected to the patient mount in a first position, for producing a visible mark in an image of the body part. A manually actuatable fastening arrangement is disposed on the assembly and/or on the patient mount for detachably fastening the assembly on the patient mount in a second position. The first and second positions are spaced from, and have a fixed relation to, one another.

14 Claims, 3 Drawing Sheets

MEDICAL TARGETING APPARATUS

BACKGROUND OF THE INVENTION

1. Field of the Invention

The present invention relates to a medical targeting apparatus of the type having an assembly composed of several parts arranged so as to be able to be displaced relative to one another, an instrument control unit connected to the assembly, adjustment means for moving the parts and the instrument control unit relative to one another, a patient mount for positioning at least a body part of a patient in a diagnostic imaging apparatus, and a marking means, connected with the patient mount in a first position, for the production of a visible mark in an image of the body part.

2. Description of the Prior Art

In minimally invasive interventions in which the target region cannot be observed directly, the use of imaging methods such as e.g. ultrasound, X-rays or magnetic resonance allows a high degree of precision to be achieved in the positioning of a corresponding instrument. The progress of the intervention is, for example, made visible continuously. The planning of an optimal access path of the instrument to the target area also can take place using previously produced images. If necessary, a natural or artificial fixed point in the area under examination can be used as a reference point.

European Application 0 752 237 discloses a mounting means for a surgical instrument is known. The mounting means has several arms that are pivotably connected with one another via joints. The entire mounting means is connected in displaceable fashion to a patient positioning means by a rail system. However, this mounting means is not provided or suitable for surgical interventions with monitoring of diagnostic tomograms.

In U.S. Pat. No. 4,629,989, a diagnostic magnetic resonance apparatus with a laser marking apparatus is described. The laser marking apparatus serves for precisely positioning an area of examination in the imaging area of the magnetic resonance apparatus.

A medical targeting apparatus of the type initially described is known from U.S. Pat. No. 5,056,523. This known targeting apparatus is provided for positioning the tip of a probe relative to a target region in a protruding body part of a patient, such as for example a female breast, with X-ray monitoring. The body part to be examined is fixed between two plates that are parallel and are transparent to radiation. One of the plates has a number of through-holes for the probe. In addition, marks that are visible in a transillumination image are present on this plate as a localization aid. Using the transillumination images, a probe guide is positioned in such a way that the probe can be guided immediately on a path to the target region. An additional scale, that is arranged coplanar to the instrument control unit and that is shown on a transillumination image, makes it possible to determine the depth of penetration.

From U.S. Pat. No. 5,678,549, a stereotactic auxiliary unit for a nuclear magnetic resonance tomography apparatus spin tomograms is known that permits a localization in a female breast of data that are visible in a magnetic resonance tomogram. The breast is thereby fixed and compressed with two compression plates. At least one of the compression plates has bored guide holes, via which a needle localization, a needle marking, or also a biopsy can be carried out with a high degree of precision. RF antennas are also allocated to the compression plates for the reception of the nuclear magnetic resonance signal.

Since in general the imaging region of the diagnostic apparatus is already filled by the patient, only a limited space is available for the adjustment of a conventional medical targeting apparatus at the patient. Particularly with magnetic resonance apparatuses, little space is available for manipulations at the targeting apparatus.

Another problem is that the adjustment of the targeting apparatus relative to the target region takes place directly at the patient. The examination time is prolonged due to the adjustment time and the preparation time, which results in a considerable burden for the patient.

SUMMARY OF THE INVENTION

An object of the present invention is to facilitate the adjustment of a medical targeting apparatus relative to the target region, and to reduce the burden for the patient caused by the adjustment.

This object is achieved in accordance with the invention in a medical targeting apparatus of the type initially described having a fastening arrangement that can be actuated manually disposed on the assembly and/or on the patient mount, for detachably fastening of the assembly on the patient mount in first and second positions, the first and the second positions been spaced from, and having are a fixed relation to, one another. It is thereby possible to carry out the adjustment of the targeting apparatus independent of the patient, on the basis of the coordinates determined in the corresponding imagings of the body part. With the inventive targeting apparatus, an adjustment can take place outside the imaging region of the diagnostic apparatus. After the adjustment has taken place, the targeting apparatus is then brought into the application position and fixed thereat. No additional adjustments are required for the examination itself.

In an one embodiment, the adjustment is made easier by providing the parts which are displaceable relative to one another with measurement scales for reading their positions relative to one another.

In another embodiment the manually actuated fastening arrangement is a snap mechanism. A mechanically simple connection of the assembly to the patient mount is thus possible that is reliable and solid, but that can be detached.

In a further embodiment, the assembly is arranged in displaceable fashion in a guide fastened to the patient mount. After the adjustment of the coordinates, the targeting apparatus is displaced on the guide into the application position.

In another embodiment, the guide is oriented in the longitudinal direction of the patient bed. The adjustment can then take place at the head end or at the foot end, and afterwards the targeting apparatus is moved to the examination position.

DESCRIPTION OF THE PREFERRED EMBODIMENTS

Figure 1:
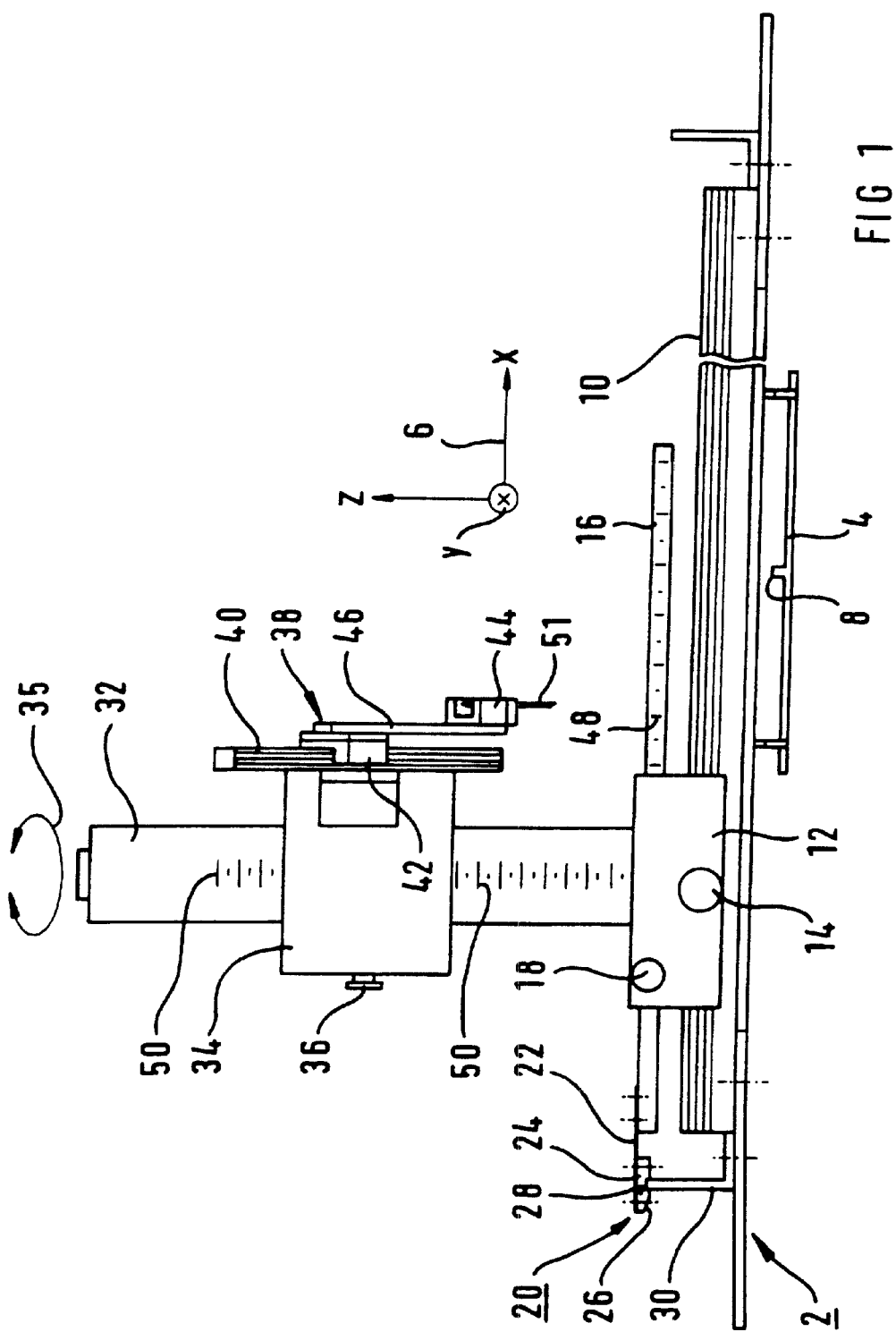
FIG. 1 is a side view of a medical targeting apparatus in accordance with the invention.

FIG. 1 shows a side view of a medical targeting apparatus that is designed for magnetic-resonance-guided interventions in a female breast. In particular, it is designed for needle localization relative to a lesion, such as for a biopsy. The apparatus is suitable, however, for any intervention in the breast, such as e.g. local radiation therapy, laser treatment, treatment with heat. Although these latter techniques are currently not yet developed to an extent to be available as standard procedures, having a targeting apparatus as described herein will assist in the progress of such development. Continuous magnetic resonance imaging makes it possible to monitor the progress of the intervention. Although in many cases magnetic resonance monitoring is the method of choice, the targeting apparatus can also be used, without limitation, together with other imaging methods, and for other anatomical regions, e.g. for bone extraction, liver punctures, muscle biopsies, etc.

Figure 2:
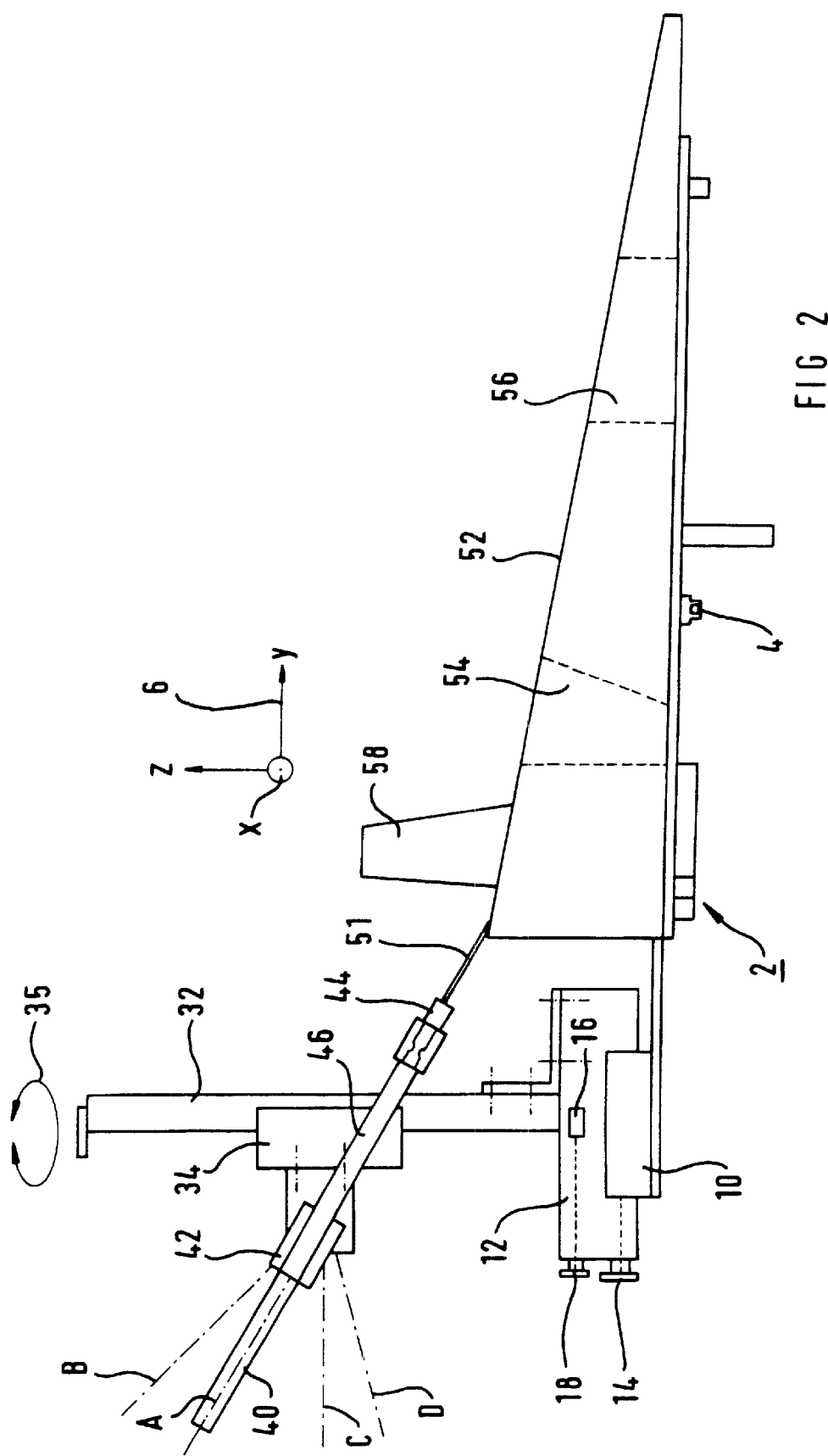
FIG. 2 is a front view of the medical targeting apparatus according to FIG. 1, with a patient positioning aid.

The targeting apparatus has a patient mount 2 for positioning at least one body part of a patient, such as a breast, that is to be examined. In FIG. 1, only one base plate is shown; additional parts of the patient mount 2 are shown in FIG. 2. The patient mount 2 can also have an arrangement for immobilizing the region of examination; however, this is not shown. The patient mount 2 is a bed in this exemplary embodiment, the view in FIG. 1 showing the longitudinal side thereof.

A marking device, in the form of a tube 4 approximately 12 cm long, is fastened to the patient mount 2. The tube 4 is fastened to the patient mount 2 in the longitudinal direction. The longitudinal direction of the tube 4 also defines the x-axis of an orthogonal (Cartesian) xyz coordinate system 6. The tube 4 also has a detent 8 that identifies the origin of the coordinate system 6. The interior of the tube 4 is filled with a substance that can be detected using magnetic resonance, e.g. gadolinium DTPA or copper sulfate. In tomograms positioned e.g. parallel to the yz plane, this substance produces marks that serve as a reference point for the determination of the y and z coordinates of a datum. A tomogram that also includes an image the detent 8 defines the zero point for the x coordinate. The x coordinate of the datum can then be determined easily from the distance of the tomogram image representing the datum to the tomogram image representing the detent 8.

A rail 10 is fastened to the patient mount 2 in the x direction, and a carriage 12 is mounted on this rail in a displaceable fashion.

The carriage 12 can be arrested on the rail 10 by a positioning screw 14, e.g. in the form of a knurled screw. An extension arm 16 is mounted in the carriage 12 so as to be displaceable in the x direction; the extension arm 16 likewise being able to be arrested in the carriage 12 by an additional positioning screw 18, e.g. in the form of a knurled screw. A spring-loaded catch 20 is fastened at one end of the extension arm 16. The spring-loaded catch 20 has an oblong spring element 22 to which a formed piece 24 is fastened. The formed piece 24 has an oblique sliding surface 26 and a recess 28. As the sliding surface 26 moves against a counterpiece 30 fastened to the patient mount 2, the catch 20 is pushed upwardly until the recess 28 engages into the counterpiece 30 in positively locking fashion.

A stationary rail 32, oriented in the z direction, is fastened to the carriage 12, and a second carriage 34 is arranged on this rail so as to be movable in the z direction and arrestable. The stationary rail 32 can be rotated on the carriage 12 around an axis oriented in the z direction, and can be arrested in 15° angular steps (indicated by the double arrow 35) in order to select the most advantageous access path. This additional degree of freedom is particularly important in the case of liver punctures. For arresting the second carriage 34 on the stationary rail 32, a knurled screw 36 is provided. An instrument control unit 38 is arranged on the second carriage 34. The instrument control unit 38 has an insert rail 40 fastened pivotably on the second carriage 34, with an insert carriage 42 being displaceably arranged on the insert rail 40. Another instrument mount 44 is fastened, via a connecting piece 46, to the insert carriage 42.

A first scale 48 is attached to the extension arm 16 on a surface thereof, here the side surface. The scale indicates the spacing in the x-direction from the zero point of the coordinate system, marked by the detent 8, when the targeting apparatus is arrested in its application position, as is shown here. A second scale 50, which is attached to a side surface of the stationary rail 32, indicates the distance of the second carriage 34 from the coordinate origin in the z direction. The penetration depth then results from the angular position of the insert rail 40, in order to reach the target coordinate values in the yz plane with an instrument fixed in the instrument holder 44, e.g. a biopsy needle 51.

FIG. 2 shows a front view of the targeting apparatus shown in FIG. 1 A positioning aid 52 that belongs to the patient mount 2, in the form of a foam wedge, is also shown. The positioning aid 52 is designed for breast examinations and has two openings 54 and 56, of which the opening 54 is fashioned so as to receive the breast to be examined and the opening 56 is fashioned so as to receive the other breast. The opening 54 is open to the side, i.e. in the direction of the targeting apparatus. Immobilization takes place with a plate (not shown here) that has openings for access by the instrument 51. A frame antenna 58 is arranged laterally in the immediate vicinity of the breast to be examined, in order to monitor the progress of the intervention with MR imaging.

The insert rail 40 is mounted so as to be able to be rotated in steps, in order to enable setting of the most advantageous access path to the target region. Four positions are provided here: the depicted position A of 30°, a steeper position B of 45°, a horizontal position C of 0°, and a position D, oriented upwards, of −15°. The path of the insert carriage 42 on the insert rail 40 can be determined from the predetermined y and z coordinates of the target, dependent on the angular position A, B, C, D of the insert rail 40, so that the instrument reaches the target region. If necessary, path (movement) limiters (not shown) can be correspondingly set on the insert rail 40.

Figure 3:
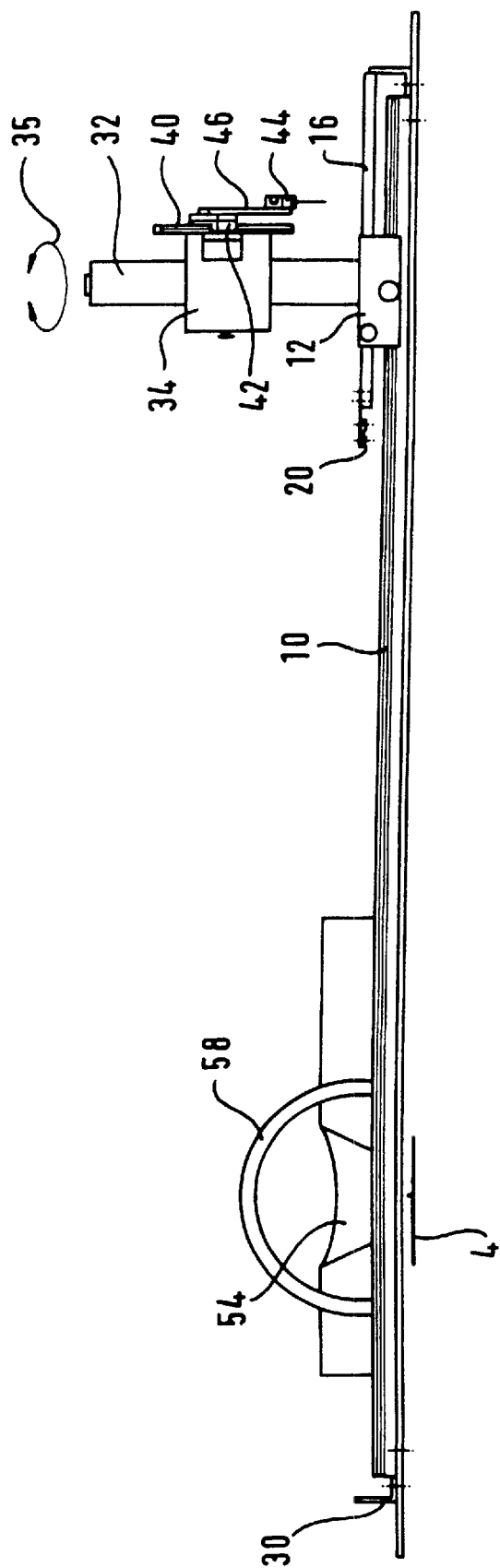
FIG. 3 shows the medical targeting apparatus according to FIG. 1 in its adjustment position.

FIG. 3 shows a side view of the medical targeting apparatus in the adjustment position. The adjustment position is e.g. at the foot end of the patient bed, outside the imaging region of the imaging apparatus. The adjustment takes place on the basis of previously recorded tomograms in which the target region, including the mark produced by the tube 4, is imaged. The x coordinate is set by the extension arm 16, and the height of the second carriage 34 in the z direction on the stationary rail 32 is set dependent on the angular position of the insert rail 40. The penetration depth is determined on the insert rail 40, e.g. with a displaceable stop (not shown). The adjusted targeting apparatus is then displaced on the rail 10 into the examination position or application position, until the counterpiece 30 engages in the recess of the spring-loaded catch 20. The targeting apparatus is thereby detachably arrested in the examination position.

Although modifications and changes may be suggested by those skilled in the art, it is the intention of the inventors to embody within the patent warranted hereon all changes and modifications as reasonably and properly come within the scope of their contribution to the art.

We claim as our invention:

1. A medical targeting apparatus comprising:

an assembly comprising a plurality of components which are mounted so as to be displaceable relative to each other;

an instrument mount adapted to hold an instrument for medical interaction with a patient, said instrument mount being attached to said assembly and being positionable relative to a patient by said assembly;

an adjustment arrangement for selectively displacing said components of said assembly to selectively position said instrument mount;

a patient mount adapted for positioning at least a body part of a patient in a diagnostic imaging apparatus;

a marker connected to said patient mount in a first position, for producing a visible mark in an image of said body part; and a manually actuatable fastener mounted on at least one of said assembly and said patient mount, for detachably fastening said assembly to said patient mount in a second position, said first position and said second position being spaced from each other and having a fixed relation to each other.

2. A medical targeting apparatus as claimed in claim 1 wherein at least some of said components of said assembly have respective measurement scales thereon for reading the respective positions of said components having said scales relative to one another.

3. A medical targeting apparatus as claimed in claim 1 wherein said manually actuatable fastening arrangement comprises a catch mechanism.

4. A medical targeting apparatus as claimed in claim 3 wherein said catch mechanism comprises a spring-loaded catch.

5. A medical targeting apparatus as claimed in claim 4 wherein said spring-loaded catch is fastened to said assembly.

6. A medical targeting apparatus as claimed in claim 5 wherein said spring-loaded catch has an opening therein, and wherein said catch mechanism further comprises a counterpiece fastened to said patient mount which engages said spring loaded catch through said opening in a positively locking fashion.

7. A medical targeting apparatus as claimed in claim 1 wherein said patient mount has a guide thereon, and wherein said assembly is displaceably mounted on said guide.

8. A medical targeting apparatus as claimed in claim 7 wherein said patient mount has a longitudinal axis, and wherein said guide is oriented substantially parallel to said longitudinal axis.

9. A medical targeting apparatus as claimed in claim 7 wherein said guide comprises a rail, and wherein said assembly includes a carriage which is mounted for sliding movement along said rail.

10. A medical targeting apparatus as claimed in claim 9 wherein said carriage comprises an arresting apparatus for fixing said carriage in a selected position along said guide.

11. A medical targeting apparatus as claimed in claim 10 wherein said apparatus comprises an extension arm mounted on said carriage so as to be displaceable relative to said carriage, and wherein said manually actuated fastening arrangement comprises fastening elements, with at least some of said fastening elements being fastened to one end of said extension arm.

12. A medical targeting apparatus as claimed in claim 9 wherein said carriage is a first carriage, and said apparatus further comprising a stationary rail on said first carriage, and a second carriage mounted on and movable along said stationary rail.

13. A medical targeting apparatus as claimed in claim 12 wherein said instrument mount comprises an insert rail rotatably mounted in said second carriage, an wherein said instrument mount includes an insert carriage that is movably mounted on said insert rail.

14. A medical targeting apparatus as claimed in claim 13 wherein said rotatably mounted insert rail is arrestable at different angular steps.

* * * * *